US005698757A

United States Patent [19]

Wu et al.

[11] Patent Number: 5,698,757
[45] Date of Patent: Dec. 16, 1997

[54] HYDRODEALKYLATION CATALYST COMPOSITION AND PROCESS THEREWITH

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 670,945

[22] Filed: Jun. 26, 1996

[51] Int. Cl.⁶ .................................................. C07C 4/12
[52] U.S. Cl. .................... 585/488; 585/488; 585/487; 585/486
[58] Field of Search .......................... 585/489, 470, 585/483, 474, 486, 475, 488; 502/61, 64, 66, 69, 67, 71, 73, 74, 77, 262, 263, 332, 334, 327; 208/107, 135, 108, 138, 109, 110, 111, 112, 118, 119, 120, 124

[56] References Cited

U.S. PATENT DOCUMENTS

| | | | |
|---|---|---|---|
| 3,308,069 | 3/1967 | Wadlinger et al. | 252/455 |
| 3,629,351 | 12/1971 | Olive et al. | 260/672 T |
| 3,890,218 | 6/1975 | Morrison | 208/135 |
| 4,188,282 | 2/1980 | Tabak et al. | 208/134 |
| 4,341,622 | 7/1982 | Tabak et al. | 208/66 |
| 4,380,685 | 4/1983 | Chu | 585/466 |
| 4,485,185 | 11/1984 | Onodera et al. | 502/71 |
| 4,548,914 | 10/1985 | Chu | 502/85 |
| 4,568,655 | 2/1986 | Oleck et al. | 502/66 |
| 4,652,360 | 3/1987 | Dessau | 208/138 |
| 4,697,039 | 9/1987 | Schmidt | 585/477 |
| 4,832,824 | 5/1989 | Vaughan et al. | 208/138 |
| 4,835,336 | 5/1989 | McCullen | 585/419 |
| 4,929,337 | 5/1990 | Herbst et al. | 208/120 |
| 5,001,296 | 3/1991 | Howley et al. | 585/489 |
| 5,030,787 | 7/1991 | Absil et al. | 585/475 |
| 5,135,643 | 8/1992 | Ward | 208/137 |
| 5,166,111 | 11/1992 | Zones et al. | 502/64 |
| 5,396,010 | 3/1995 | Harandi et al. | 585/418 |
| 5,399,258 | 3/1995 | Fletcher et al. | 208/89 |
| 5,411,658 | 5/1995 | Chawla et al. | 208/89 |

FOREIGN PATENT DOCUMENTS 03025791 2/1991 Japan .

OTHER PUBLICATIONS

N. Chen and T. Yan, *Ind. Eng. Chem. Proc. Des. Dev.* 25:151-155 (1986).
N. Guisnet et al, *Appl. Cataly. A: General* 87:255-270 (1992).
Kirk-Other Encyclopedia of Chemical Technology, 3rd edition, vol. 15, pp. 638-669 (1981).

*Primary Examiner*—Glenn A. Caldarola
*Assistant Examiner*—Thuan D. Dang
*Attorney, Agent, or Firm*—Lucas K. Shay

[57] ABSTRACT

A composition which comprises a platinum-promoted zeolite and a gallium-promoted zeolite is disclosed. The composition can be used for converting a $C_9+$ aromatic compound to a $C_6$ to $C_8$ aromatic hydrocarbon. Also disclosed is a process for converting a $C_9+$ aromatic compound to a $C_6$ to $C_8$ aromatic hydrocarbons employing the composition.

30 Claims, No Drawings

5,698,757

HYDRODEALKYLATION CATALYST COMPOSITION AND PROCESS THEREWITH

FIELD OF THE INVENTION

This invention relates to a catalyst composition which can be used for converting $C_9+$ aromatic compounds to $C_6$ to $C_8$ aromatic hydrocarbons and to a process for using the composition.

BACKGROUND OF THE INVENTION

It is well known to one skilled in the art that aromatic hydrocarbons, especially those having 6 to 8 carbons, are a class of important industrial chemicals which find a variety of uses in petrochemical industry. Recent efforts to convert gasoline to more valuable petrochemical products have therefore focused on the conversion of gasoline to aromatic hydrocarbons by catalytic cracking in the presence of zeolite catalysts. The aromatic hydrocarbons produced by such conversion processes include benzene, toluene and xylenes (hereinafter collectively referred to as BTX or $C_6$ to $C_8$ hydrocarbons), which can be useful feedstocks for producing various organic compounds and polymers. However, heavier, less useful aromatic compounds are also produced by such conversion processes. Therefore, development of a catalyst and a process for converting these heavier aromatic compounds (mainly trimethyl- and tetramethylbenzenes) to the more valuable BTX hydrocarbons would be a significant contribution to the art and to the economy.

SUMMARY OF THE INVENTION

An object of this invention is to provide a catalyst composition which can be used to convert $C_9+$ aromatic compounds to $C_6$ to $C_8$ aromatic hydrocarbons. Another object of this invention is to provide a process which can employ the catalyst composition to convert $C_9+$ aromatic hydrocarbons to $C_6$ to $C_8$ aromatic compounds. An advantage of the catalyst composition is that it exhibits high hydrodealkylation activity, satisfactory selectivity to xylenes, and good stability. Other objects and advantages will becomes more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition comprises, consists essentially of, or consists of, (a) a platinum-promoted zeolite and (b) a gallium-promoted zeolite.

According to a second embodiment of the present invention, a process which can be used for converting a $C_9+$ aromatic compound to a $C_6$ to $C_8$ aromatics compound is provided which comprises, consists essentially of, or consists of, contacting a fluid which comprises a $C_9+$ aromatic compound with a hydrogen-containing fluid in the presence of a catalyst composition which comprises, consists essentially of, or consists of, (a) a platinum-promoted zeolite and (b) a gallium-promoted zeolite under a condition effective to convert the a $C_9+$ aromatic compound to an aromatic hydrocarbon containing 6 to 8 carbon atoms per molecule.

DETAILED DESCRIPTION OF THE INVENTION

The catalyst composition of the first embodiment oft he present invention comprises, consists essentially of, or consists of (a) platinum-promoted zeolite and (b) a gallium-promoted zeolite. The weight ratio of the platinum-promoted zeolite to the gallium-promoted zeolite can be any ratio so long as the ratio can effectively convert a $C_9+$ aromatic compound to a $C_6$ to $C_8$ aromatic hydrocarbon. Generally, the ratio of the platinum-promoted zeolite to the gallium-promoted zeolite can be in the range of from about 0.001:1 to about 200:1, preferably abut 0.01:1 to about 100:1, more preferably about 0.1:1 to about 10:1, and most preferably 0.15:1 to 6:1.

Generally, any weight percent (%) of platinum in the platinum-promoted zeolite component can be used as long as the weight % can effect the conversion of a $C_9+$ aromatic compound to a $C_6$ to $C_8$ aromatic hydrocarbon. The weight % of platinum in the platinum-promoted zeolite can be in the range of from about 0.001 to about 10, preferably about 0.01 to about 5, and most preferably 0.1 to 2% based on the weight of the platinum-promoted zeolite equaling 100%. Similarly, and weight % of gallium in the gallium-promoted zeolite can be used so long as the weight % can effect the conversion of $C_9+$ aromatic compound to a $C_6$ to $C_8$ aromatic hydrocarbon. Generally, the weight % of gallium in the gallium-promoted zeolite can be in the range of from about 0.001 to about 10, preferably about 0.01 to about 5, and most preferably 0.1 to 2% based on the total weight of the gallium-promoted zeolite being 100%.

Although any zeolite known to one skilled in the art can be employed in the present invention, it is preferred that a zeolite Beta be used in the platinum-promoted zeolite. A zeolite Beta as described in U.S. Pat. No. 3,308,069, having a $SiO_2:Al_2O_3$ molar ratio in the range of from about 5:1 to about 50:1 is particularly preferred. Such a zeolite Beta can also contain (a) boron and/or other metals such as, for example, In, Zn, Cr, Ge, Sn, and combinations of any two or more thereof; (b) nickel (as Ni metal or at least one nickel compound or combinations of two or more thereof); (c) molybdenum (as Mo metal or at least one molybdenum compound or mixtures thereof), and (d) sulfur (as sulfide). A zeolite can further comprise an inorganic binder, such as alumina, silica, alumina-silica, aluminum phosphate, clay such as, for example, bentonite, and combinations of any two or more thereof. The presently preferred binder is an alumina.

Generally, any platinum-containing compound that can promote the combining of platinum element with an aluminosilicate can be employed herein. Examples of suitable platinum-containing compounds include, but are not limited to, chloroplatinic acid ($H_2PtCl_6 \cdot xH_2O$), platinum (IV) chloride (platinic chloride), platinum (II) bromide, platinum (II) iodine, tetramine platinum (II) chloride ($Pt(NH_3)_4Cl_2 \cdot H_2O$ or $Pt(NH_3)_4Cl_2$), tetramine platinum (II) nitrate ($Pt(NH_3)_4(NO_3)_2$), tetramine platinum (II) hydroxide ($Pt(NH_3)_4(OH)_2$), tetrachlorodiamine platinum (IV), and combinations of any two or more thereof. The presently preferred platinum-containing compound is chloroplatinic acid for it is readily available.

A platinum-promoted zeolite can be prepared by any suitable, effective means so long as the resulting zeolite can be used in the process of the present invention. Preferably, a zeolite material, which can have been compounded with a binder as described above and have been shaped by any means known in the art such as, for example, pelletized, extruded, tableted, or combinations of two or more thereof, can be first impregnated such as, for example, by incipient wetness method with a solution, preferably aqueous solution, containing a suitable platinum-containing compound disclosed above. The concentrations of the platinum-containing compound in the impregnating solution and the weight ratio of this solution to the zeolite are chosen such as to provide a finished, platinum-impregnated zeolite which contains the desired content of platinum as disclosed above.

After the impregnation with a platinum compound has been completed, the platinum-impregnated zeolite can then be dried and calcined. Generally the calcination is carried out in air at a temperature in the range of about 300° to about 1000° C. for about 1 to about 20 hours, preferably about 400° C. to about 800° C. for 2 to about 15 hours, and most preferably 450° C. to 650° C. for 3 to 10 hours.

The calcined platinum-impregnated zeolite can then be treated with a reducing agent to reduce the oxidation state of platinum to 0. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 550° C. for 1 to 5 hours. If the calcined platinum-impregnated zeolite is not first treated with a reducing agent, the composition of the present invention can be treated with a reducing agent as described herein prior to use of the composition of the invention.

Upon completion of the above-described treatments of a zeolite with a platinum-containing compound, a platinum-zeolite composition is produced which can then be combined with a gallium-promoted zeolite.

Similarly, although any zeolite known to one skilled in the art can be used in the present invention for producing a gallium-promoted zeolite, it is presently preferred that a ZSM-5 zeolite and similar zeolites that have been identified as having a framework topology identified as MFI be employed.

Any gallium-containing compound that can effect the production of gallium-promoted zeolite can be used herein. Examples of suitable gallium-containing compounds include, but are not limited to, gallium acetate (basic), gallium trifluoride, gallium trichloride, gallium, gallium hydroxide, gallium nitrate, gallium sulfate, and combinations of any two or more thereof.

A gallium-promoted zeolite can be prepared by any suitable, effective means so long as the resulting zeolite can be used in the process of the present invention. Preferably, a zeolite material, which can have been compounded with a binder as described above and have been shaped by any means known in the art such as, for example, pelletized, extruded, tableted, or combinations of two or more thereof, can be first impregnated such as, for example, by incipient wetness method with a solution, preferably aqueous solution, containing a suitable gallium-containing compound disclosed above. The concentrations of the gallium-containing compound in the impregnating solution and the weight ratio of this solution to the zeolite are chosen such as to provide a finished, gallium-impregnated zeolite which contains the desired content of gallium as disclosed above.

After the impregnation with a gallium compound has been completed, the gallium-impregnated zeolite can then be dried and calcined. Generally the calcination is carried out in air at a temperature in the range of about 300° to about 1000° C. for about 1 to about 20 hours, preferably about 400° C. to about 800° C. for 2 to about 15 hours, and most preferably 450° C. to 650° C. for 3 to 10 hours.

The composition of the present invention can then be produced by physically combining any desired weight ratios of the platinum-promoted zeolite and the gallium-promoted zeolite which are each prepared as described above. Any methods known to one skilled in the art such as, for example, dry blending or mixing, wet mixing followed by drying and calcining, extruding, can be employed. Because these methods are well known to one skilled in the art, description of which is omitted herein.

According to the second embodiment of the present invention, a process useful for converting a $C_9$+ aromatic compound to a $C_6$ to $C_8$ aromatic hydrocarbon comprises, consists essentially of, or consists of contacting a fluid stream comprising a $C_9$+ aromatic compound, in the presence of a catalyst composition, with a hydrogen-containing fluid. The catalyst composition is the same as that disclosed in the first embodiment of the invention.

According to the present invention, the term "fluid" is used herein to denote gas, liquid, vapor, or combinations of two or more thereof. The term "$C_9$+ aromatic compound" is referred to, unless otherwise indicated, as a substituted aromatic compound containing at least 9 carbon atoms per molecule. Preferably the substituted aromatic compound has the formula of $R_nAr$ wherein each R is a hydrocarbyl radical having 1 to about 15 carbon atoms and is independently selected from the group consisting of alkyl radicals, aryl radicals, alkaryl radicals, aralkyl radicals, and combinations of any two or more thereof. n is a whole number from 1 to 5, and Ar is a phenyl group. More preferably R is an alkyl radical having 1 to about 10 carbon atoms and the aromatic compound has 9 to about 16 carbon atoms per molecule. Most preferably, the aromatic compound contains 9 to 12 carbon atoms per molecule.

Any fluid which contains a $C_9$+ aromatic compound as disclosed above can be used as the feed for the process of this invention. The origin of this feed is not critical. However, a preferred fluid feed is a $C_9$+ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, and 1,3-diethylbenzene can also be present in the fluid. Benzene, toluene, ethylbenzene and xylenes are generally substantially absent from the fluid, i.e., the amount of each of these aromatic hydrocarbons is less than about 0.1 weight %. Thus, no significant alkylation of these lower aromatic hydrocarbons by the $C_9$+ aromatic compound, i.e., no significant transalkylation occurs as a side-reaction in the process of this invention.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, or combinations of any two or more thereof, or any other fluid which does not significantly affect the process or the catalyst composition used therein.

The contacting of a fluid containing a $C_9$+ aromatic compound and a hydrogen-containing fluid in the presence of the catalyst composition can be carried out in any technically suitable manner under a condition effective to convert a $C_9+$ aromatic compound to a $C_6$ to $C_8$ aromatic hydrocarbon. Generally, a fluid containing a $C_9+$ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9+$ aromatic compound fluid stream in the range of about 0.01 to about 100, preferably about 0.05 to about 50, and most preferably 0.1 to 30 g feed/g catalyst/hour. The hydrogen-containing fluid (gas) hourly space velocity generally is in the range of about 1 to about 10,000, preferably about 5 to about 7,000, and most preferably 10 to 5,000 ft$^3$ H$_2$/ft$^3$ catalyst/hour. The preferred molar ratio of $H_2$ to the $C_9+$ aromatic compound can be in the range of from about 0.01:1 to about 20:1, preferably about 0.1:1 to about 10:1, and most preferably 0.5:1 to 5:1. Generally, the pressure can be in he range of from about 30 to about 1000 psig, preferably about 50 to 750 psig, and most preferably 200 to 600 psig, and the temperature can be about 250° to about 1,000° C., preferably about 350° to about 750° C., and most preferably 450° to 650° C.

The process effluent generally contains a heavies fraction of unconverted $C_9+$ aromatics and other heavy ($C_9+$) aromatics which may have been formed by side-reactions (such as isomerization); a lights fraction of alkanes, mainly methane, ethane, propane, n-butane, isobutane, and minor amounts (about 0.1 to about 5 weight %) of $C_8$ alkanes (isopentane and n-pentane); and a BTX aromatic hydrocarbons (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor described above, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes) involving transalkylation benzene and xylenes (to form toluene), and isomerization of meta-xylene and/or ortho-xylene to para-xylene.

After the catalyst composition has been deactivated, by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400° to about 650° C., followed by a treatment with a reducing agent such as, for example, with hydrogen gas at a temperature of about 400° to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the preparation of catalyst composition of the present invention. All catalyst preparations comprise impregnation of a zeolite by incipient wetness method at room temperature (about 25° C.).

Catalyst A (Control) was a platinum-promoted zeolite Beta material which was prepared by impregnating 36.0 grams of a zeolite Beta (1/16" extrudates; obtained from UOP Inc., Des Plains, Ill. under the product designation "MD-08318-69, DR #3") with 0.40 gram of chloroplatinic acid (H$_2$PtCl$_4$.xH$_2$O) in a solution of nitric acid (0.40 g HNO$_3$ and 23.27 g H$_2$O) followed by drying for 3 hours in air at 125° C. to produce a platinum-impregnated zeolite Beta. The platinum-impregnated zeolite Beta was then calcined for 6 hours in air at 525° C. to produce a platinum-promoted zeolite Beta. Catalyst A contained 0.424 weight % of platinum. In this preparation, the platinum-promoted Zeolite Beta was further treated with a flowing hydrogen gas at 260 ml of H$_2$ per minute for 2 hours at 425° C. in a, Catalyst B (Control) was a gallium-promoted ZSM-5 zeolite prepared by impregnating 22.0 grams of ZSM-5 (obtained from UCI; United Catalysts, Inc., Louiville, Ky., having a designate of T-4480) with 1.50 grams of gallium nitrate (Ga(NO$_3$)$_3$.9H$_2$O) in 9.0 grams of nitric acid having a pH of 1.50 followed by drying in air at 125° C. for 3 hours to prepare a gallium-impregnated ZSM-5. The gallium-impregnated ZSM-5 was then calcined for 6 hours in air at 525° C. to prepare a gallium-promoted ZSM-5 zeolite. Catalyst B contained 1.174 weight % of gallium.

The invention catalysts were prepared by physically combining or mixing or hybridizing catalyst A and catalyst B in weight ratios shown in Table II.

The compositions described above were used in a hydrodealkylation of $C_9+$ aromatic compounds to BTX. The hydrodealkylation was carried out as follows.

A stainless-steel reactor tube (inner diameter 0.75 inch; length: 20 inches) was filled with a 5 cc bottom layer of Alundum® alumina (inert, low surface area alumina) 10 cc of one of the catalysts, and a 5 cc top layer of Alundum® alumina. (The catalyst should be pretreated with flowing hydrogen gas (flow rate: 260 cc H$_2$ per minute), if the platinum-promoted zeolite had not previously been treated with a reducing agent, at a temperature being raised from room temperature to a final temperature of 450° C. at a rate of 10° C. per minute.) Then a liquid feed which contained $C_9+$ aromatic hydrocarbons was introduced at a rate of 40 cc/hour, together with hydrogen gas at a rate of 260 cc H$_2$/minute. The liquid hourly space velocity of the feed was about 4 cc feed/cc catalyst/hour (equivalent to a weight hourly space velocity of about 5.5–6 g feed/g catalyst/hour). The reaction temperature was 550° C. and the pressure was 500 psig. The reactor effluent was cooled and separated into a gaseous phase and a liquid phase. Both phases were analyzed by gas chromatographs at intervals of about 1 hour.

The liquid feed in the runs was a mixture of heavy $C_9+$ aromatic compounds obtained in a gasoline aromatization test. The composition of the feed is given in Table I, the sulfur content in this feed was less than 2 ppm S. It should be noted that numerous components which were in low concentrations and, in some instances, were unidentified are not included in Table I. Pertinent hydrodealkylation test results are summarized in Table II.

TABLE I

Composition of Feed

| Feed Component | Weight Percent |
| --- | --- |
| c-Hexene-2 | 1.104 |
| 1-Methyl-3-ethylbenzene | 2.254 |
| 1-Methyl-4-ethylbenzene | 1.057 |
| 1,3,5-Trimethylbenzene | 1.958 |
| 1-Methyl-2-ethylbenzene | 1.306 |
| 1,2,4-Trimethylbenzene | 9.977 |
| 1,2,3-Trimethylbenzene | 3.060 |
| 1-Methyl-3-i-propylbenzene | 0.286 |
| 2,3-Dihydroindene | 2.845 |
| 1,3-Diethylbenzene | 1.173 |
| 1-Methyl-3-n-propylbenzene | 1.543 |
| 1,4-Diethylbenzeneylbenzene | 0.910 |
| 1-Methyl-4-n-propylbenzene | 0.328 |
| n-Butylbenzene-ethylbenzene | 2.836 |
| 1-Methyl-2-n-propylbenzene | 0.889 |
| 1,4-Dimethyl-2-ethylbenzene | 1.991 |
| s-C5-benzene/1,3-dimethyl-4-ethylbenzene | 2.958 |
| 1,2-Dimethyl-4-ethylbenzene | 3.454 |
| 1,2-Dimethyl-3-ethylbenzene | 1.007 |
| 1,2,4,5-Tetramethylbenzene | 1.936 |
| 1,2,3,5-Tetramethylbenzene | 2.695 |
| 5-Methylindan | 3.004 |
| 1 Ethyl-2-n-propylbenzene | 1.592 |
| 2-Methylindan | 3.040 |
| 1,3-Di-i-propylbenzene | 1.084 |
| Naphthalene | 4.767 |
| 2-Methylnaphthalene | 3.382 |
| 1-Methylnaphthalene | 1.184 |

TABLE II

Conversion of $C_9$+ Aromatic Compounds[a]

| Run Number | Catalyst (g) A | Catalyst (g) B | Conversion of $C_9$+[b] (%) | Weight % of $C_9$+[b] | Weight % of Xylenes | Weight % of BTX |
| --- | --- | --- | --- | --- | --- | --- |
| 1 | 11.87 | 0 | 47.0 | 30.8 | 4.8 | 39.9 |
| 2 | 0 | 11.87 | 59.3 | 23.7 | 14.9 | 49.0 |
| 3 | 5.30 | 6.57 | 74.7 | 14.7 | 18.1 | 60.4 |
| 4 | 9.89 | 1.98 | 60.1 | 23.2 | 17.8 | 51.1 |
| 5 | 7.91 | 3.96 | 66.5 | 19.5 | 18.3 | 55.9 |
| 6 | 3.96 | 7.91 | 66.8 | 19.6 | 18.4 | 58.3 |
| 7 | 1.98 | 9.89 | 62.4 | 21.9 | 18.7 | 56.0 |

[a]The values shown for % conversion of $C_9$ and weight % of xylenes and BTX were obtained at 6.75 hours (runs 1 and 2), 5.86 hours (run 3), 6 hours (runs 4 and 7), 6.5 hours (run 5), or 6.25 hours (run 6) after the runs were started.
[b]$C_9$+ = $C_9$+ aromatic compounds.

Test results in Table II clearly demonstrate that the conversion and weight % of desired xylenes for invention runs 2 to 7 were significantly higher than those for the control runs 1 and 3. Table II further demonstrates that the invention runs, as compared to the control runs, had lower content of $C_9$+ aromatic hydrocarbons in the reactor effluent, i.e., higher conversion of the feed to BTX.

Reasonable variations, modifications and adaptations for various usages and conditions can be made within the scope of the disclosure and the appended claims, without departing from the scope of this invention.

That which is claimed:

1. A process comprising contacting, in the presence of a catalyst composition, a fluid which comprises a $C_9$+ aromatic compound with a hydrogen-containing fluid under a condition effective to convert a $C_9$+ aromatic compound to a $C_6$ to $C_8$ aromatic hydrocarbon wherein said catalyst composition comprises an effective ratio of (1) platinum-promoted zeolite and (2) gallium-promoted zeolite wherein said ratio is effective to convert a $C_9$+ aromatic compound to a $C_6$ to $C_8$ aromatic hydrocarbon; the zeolite in said platinum-promoted zeolite is zeolite Beta; and the zeolite in said gallium-promoted zeolite is ZSM-5 zeolite.

2. A process according to claim 1 wherein the weight ratio of said platinum-promoted zeolite to gallium-promoted zeolite is in the range of from about 0.01:1 to about 100:1.

3. A process according to claim 1 wherein the weight ratio of said platinum-promoted zeolite to gallium-promoted zeolite is in the range of from about 0.1:1 to about 10:1.

4. A process according to claim 1 wherein the weight ratio of said platinum-promoted zeolite to gallium-promoted zeolite is in the range of from 0.15:1 to 6:1.

5. A process according to claim 1 wherein the weight ratio of platinum to zeolite in said platinum-promoted zeolite is in the range of from about 0.0001:1 to about 0.1:1.

6. A process according to claim 1 wherein the weight ratio of platinum to zeolite in said platinum-promoted zeolite is in the range of from 0.001:1 to 0.01:1.

7. A process according to claim 1 wherein the weight ratio of gallium to zeolite in said gallium-promoted zeolite is in the range of from 0.0001:1 to about 0.1:1.

8. A process according to claim 1 wherein the weight ratio of gallium to zeolite in said gallium-promoted zeolite is in the range of from 0.001:1 to 0.05:1.

9. A process according to claim 1 wherein said composition comprises components of (1) a platinum-promoted zeolite Beta and (2) a gallium-promoted ZSM-5 zeolite wherein the weight ratio of platinum-promoted zeolite Beta to gallium-promoted ZSM-5 zeolite is in the range of from about 0.0001:1 to about 200:1; the weight ratio of platinum to zeolite Beta is in the range of from about 0.0001:1 to about 0.1:1; and the weight ratio of gallium to ZSM-5 zeolite is in the range of from about 0.0001:1 to about 0.1:1.

10. A process according to claim 9 wherein the weight ratio of said platinum-promoted zeolite Beta to gallium-promoted ZSM zeolite is in the range of from about 0.1:1 to about 10:1.

11. A process according to claim 9 wherein the weight ratio of said platinum-promoted zeolite Beta to gallium-promoted ZSM zeolite is in the range of from 0.15:1 to 6:1; the weight ratio of platinum to zeolite Beta is in the range of from 0.001:1 to 0.01:1; and the weight ratio of gallium to ZSM-5 zeolite is in the range of 0.001:1 to 0.05:1.

12. A process according to claim 1 wherein said catalyst composition comprises an inorganic binder selected from the group consisting of alumina, silica, alumina-silica, aluminum phosphate and clay.

13. A process according to claim 12 wherein said inorganic binder is present in said catalyst composition in the range of from about 1 to about 40 weight %.

14. A process according to claim 1 wherein said condition comprises a weight hourly space velocity of said fluid in the range of 0.1 to 30 g feed/g catalyst/hour, a gas hourly space velocity of said hydrogen-containing fluid in the range of about 10 to about 5,000 ft$^3$/ft$^3$ catalyst/hour, a molar ratio of hydrogen to said $C_9$+ aromatic compound in the range of about 0.5:1 to about 5:1, a pressure in the range of about 50 psig to about 750 psig, and a temperature in the range of about 250° C. to about 1,000° C.

15. A process according to claim 14 wherein said condition comprises a pressure of about 200 to about 600 psig and a temperature of 450° to 650° C.

16. A process according to claim 1 wherein said $C_9$+ aromatic compound comprises an aromatic hydrocarbon selected from the group consisting of 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, and combinations of any two or more thereof.

17. A process comprising contacting, in the presence of a catalyst composition, a fluid which comprises a $C_9+$ aromatic compound with a hydrogen-containing fluid under a condition effective to convert a $C_9+$ aromatic compound to a $C_6$ to $C_8$ aromatic hydrocarbon wherein said catalyst composition comprises an effective ratio of (1) platinum-promoted zeolite Beta and (2) gallium-promoted ZSM-5 zeolite wherein said ratio is effective to convert a $C_9+$ aromatic compound to a $C_6$ to $C_8$ aromatic hydrocarbon; and the weight ratio of said platinum-promoted zeolite Beta to said gallium-promoted ZSM-5 zeolite is in the range of from about 0.01:1 to about 100:1.

18. A process according to claim 17 wherein the weight ratio of platinum to zeolite in said platinum-promoted zeolite is in the range of from 0.001:1 to 0.01:1.

19. A process according to claim 17 wherein the weight ratio of gallium to zeolite in said gallium-promoted zeolite is in the range of from 0.001:1 to 0.05:1.

20. A process according to claim 17 wherein said composition comprises components of (1) a platinum-promoted zeolite Beta and (2) a gallium-promoted ZSM-5 zeolite wherein the weight ratio of platinum-promoted zeolite Beta to gallium-promoted ZSM-5 zeolite is in the range of from about 0.0001:1 to about 200:1; the weight ratio of platinum to zeolite Beta is in the range of from about 0.0001:1 to about 0.1:1; and the weight ratio of gallium to ZSM-5 zeolite is in the range of from about 0.0001:1 to about 0.1:1.

21. A process according to claim 20 wherein the weight ratio of said platinum-promoted zeolite Beta to gallium-promoted ZSM zeolite is in the range of from about 0.1:1 to about 10:1.

22. A process according to claim 21 wherein the weight ratio of said platinum-promoted zeolite Beta to gallium-promoted ZSM zeolite is in the range of from 0.15:1 to 6:1; the weight ratio of platinum to zeolite Beta is in the range of from 0.001:1 to 0.01:1; and the weight ratio of gallium to ZSM-5 zeolite is in the range of 0.001:1 to 0.05:1.

23. A process according to claim 17 wherein said catalyst composition comprises an inorganic binder selected from the group consisting of alumina, silica, alumina-silica, aluminum phosphate and clay.

24. A process according to claim 23 wherein said inorganic binder is present in said catalyst composition in the range of from about 1 to about 40 weight %.

25. A process according to claim 17 wherein said condition comprises a weight hourly space velocity of said fluid in the range of 0.1 to 30 g feed/g catalyst/hour, a gas hourly space velocity of said hydrogen-containing fluid in the range of about 10 to about 5,000 ft$^3$/ft$^3$ catalyst/hour, a molar ratio of hydrogen to said $C_9+$ aromatic compound in the range of about 0.5:1 to about 5:1, a pressure in the range of about 50 psig to about 750 psig, and a temperature in the range of about 250° C. to about 1,000° C.

26. A process according to claim 25 wherein said condition comprises a pressure of about 200 to about 600 psig and a temperature of 450° to 650° C.

27. A process comprising contacting, in the presence of a catalyst composition, a fluid which comprises a $C_9+$ aromatic compound with a hydrogen-containing fluid under a condition effective to convert a $C_9+$ aromatic compound to a $C_6$ to $C_8$ aromatic hydrocarbon composition comprises components of (1) a platinum-promoted zeolite Beta and (2) a gallium-promoted ZSM-5 zeolite wherein the weight ratio of said platinum-promoted zeolite Beta to gallium-promoted ZSM-5 zeolite is in the range of from about 0.0001:1 to about 200:1; the weight ratio of platinum to zeolite Beta is in the range of from about 0.0001:1 to about 0.1:1; and the weight ratio of gallium to ZSM-5 zeolite is in the range of from about 0.0001:1 to about 0.1:1.

28. A process according to claim 27 wherein the weight ratio of platinum-promoted zeolite Beta to gallium-promoted ZSM-5 zeolite is in the range of from about 0.1:1 to about 10:1.

29. A process according to claim 27 wherein the weight ratio of platinum-promoted zeolite Beta to gallium-promoted ZSM-5 zeolite is in the range of from 0.15:1 to 6:1; the weight ratio of platinum to zeolite Beta is in the range of from 0.001:1 to 0.01:1; and the weight ratio of gallium to ZSM-5 zeolite is in the range of 0.001:1 to 0.05:1.

30. A process comprising contacting, in the presence of a catalyst composition, a fluid which comprises a $C_9+$ aromatic compound with a hydrogen-containing fluid under a condition effective to convert a $C_9+$ aromatic compound to a $C_6$ to $C_8$ aromatic hydrocarbon composition comprises components (1) platinum-promoted zeolite Beta and (2) gallium-promoted ZSM-5 zeolite wherein the weight ratio of platinum-promoted zeolite Beta to gallium-promoted ZSM-5 zeolite is in the range of from 0.15:1 to 6:1; the weight ratio of platinum to zeolite Beta is in the range of from 0.001:1 to 0.01:1; the weight ratio of gallium to ZSM-5 zeolite is in the range of from 0.001:1 to 0.05:1; and said condition comprises a weight hourly space velocity of said fluid in the range of 0.1 to 30 g feed/g catalyst/hour, a gas hourly space velocity of said hydrogen-containing fluid in the range of about 10 to about 5,000 ft$^3$/ft$^3$ catalyst/hour, a molar ratio of hydrogen to said $C_9+$ aromatic compound in the range of about 0.5:1 to about 5:1, a pressure in the range of about 50 psig to about 750 psig, and a temperature in the range of about 250° C. to about 1,000° C.

* * * * *